United States Patent
Bourgelas (10) Patent No.: US 9,390,520 B2
(45) Date of Patent: Jul. 12, 2016

(54) METHOD AND SYSTEM OF SIGNAL REPRESENTATION FOR NDT/NDI DEVICES

(71) Applicant: Tommy Bourgelas, Shannon (CA)

(72) Inventor: Tommy Bourgelas, Shannon (CA)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 370 days.

(21) Appl. No.: 13/967,690

(22) Filed: Aug. 15, 2013

(65) Prior Publication Data
US 2015/0049108 A1    Feb. 19, 2015

(51) Int. Cl.
*G06T 7/00* (2006.01)
*G06T 11/00* (2006.01)
*G01N 29/11* (2006.01)
*G01B 11/24* (2006.01)

(52) U.S. Cl.
CPC .............. *G06T 11/001* (2013.01); *G01N 29/11* (2013.01); *G06T 7/0004* (2013.01); *G01B 11/24* (2013.01); *G06T 2207/10132* (2013.01)

(58) Field of Classification Search
CPC ..................... G01N 29/11; G06T 2207/10132; G06T 7/0004; G01B 11/24
See application file for complete search history.

(56) References Cited

U.S. PATENT DOCUMENTS

2007/0217672 A1*  9/2007  Shannon ............... G06T 7/0006
                                              382/152
2011/0118991 A1*  5/2011  Lepage ................ G01N 29/075
                                              702/39

\* cited by examiner

*Primary Examiner* — Matthew Salvucci
(74) *Attorney, Agent, or Firm* — C. Trica Liu (57) ABSTRACT

Disclosed is a method and system to provide an improved signal representation of non-destructive test/inspection instruments by proper color display, in order to emulate as closely as possible, the visual rendering effect of those seen in the traditional non-electronic testing, including penetrant testing and magnetic particle testing. The foregoing object of the invention is preferably realized by providing an eddy current or phased array instrument with a color palette module that allows the deployment of an array of color representation system typically used in traditional non-electronic testing methods.

19 Claims, 6 Drawing Sheets
(4 of 6 Drawing Sheet(s) Filed in Color)

PT / VISIBLE / RED DYE with PINK SHADES

PT / VISIBLE / RED DYE with PINK SHADES

Fig. 3

PT / FLUORESCENT / BLUE-GREEN

Fig. 4

MP / FLUORESCENT / PURPLE SHADES

Fig. 5

MP / VISIBLE / RED POWDER

METHOD AND SYSTEM OF SIGNAL REPRESENTATION FOR NDT/NDI DEVICES

FIELD OF THE INVENTION

The present invention relates to non-destructive testing and inspection devices (NDT/NDI) and more particularly to the usage of color representation of signals generated by the NDT/NDI devices, emulating the color representations typically used by a few traditional, non-electronic testing methods, such as penetrant testing (herein after as "PT"), and magnetic particle (herein after as "MP").

BACKGROUND OF THE INVENTION

Typically traditional, non-electronic NDT methods involve usage of test materials with color or florescence property, which either leak or change patterns of distribution around flaws or defects. The NDT industry has formed certain conventions in using certain colors and florescence involving these traditional methods.

Modern instruments using array probe technologies, including eddy current array (ECA) and ultrasonic phased array (PA) technologies, with color imaging capability and its ability to detect surface-breaking or near-surface flaws through relatively thin coatings, are ideal replacements to traditional, non-electronic NDT methods for productivity reasons as traditional methods require intensive surface preparation, coating removal (and re-application after test), and have no direct means to record archive results apart from taking on-site pictures.

Eddy Current Array technology detects most flaws found by the traditional methods, and returns a color image (the C-scan) displaying colors as function of a signal amplitude or phase. In the existing market, the color schemes employed with ECA technology was done by various manufacturers using rainbow-style color palettes, typically comprising green/blue as base color, then shades of green, red, yellow. In contrast, traditional NDT methods such as penetrant testing (PT) and Magnetic particle (MP), either visible or fluorescent, provide characteristic visual images where flaws show up in a color tone much different from the background color representing non-defect zones.

Examples of visible penetrant testing include red tone and pink/purple tone. Red tone testing has a background (good part) of white/light gray, and flaws highlighted with bright red tones Pink/purple tone testing has a background (good part) of white/light gray, and flaws highlighted with pink/purple tones.

Examples of fluorescent penetrant testing, which is performed in a dark room with a "black light", include green/blue shades and purple/blue shades. Green/blue shades typically have a background of dark blue tones and flaws glow as bright green shades (fluorescent). Purple/blue shades typically have a background of dark purple tones and flaws glow as light blue shades (fluorescent).

Examples of visible magnetic particle testing include red and black powder testing. The background color of red and black powder testing, which can vary depending of the surface being tested, shows better contrast when it is pale. The red and black powder will reveal the defects as the powders cling to the flaw edges.

Examples of fluorescent magnetic particle testing include purple shades and blue shades. Fluorescent magnetic particle testing is performed in a dark room with a "black light". In purple shades the UV lamp typically produces purple reflects on the background color and flaws glow bright blue-green as the fluorescent magnetic particles cling to the flaw edges. In blue shades the UV lamp typically produces blue reflects on the background color and flaws glow bright blue-green as the fluorescent magnetic particles cling to the flaw edges.

Understandably, it is desirable to provide modern instruments, such as eddy current array technologies with the capability of displaying colors or florescence in the similar fashion as those traditional, non-electronic NDT method does.

SUMMARY OF THE INVENTION

A primary object of the present disclosure is to provide a method offering improved signal representation of NDT/NDI instruments by proper color display, in order to emulate as closely as possible, the visual rendering effect of those seen in the traditional non-electronic testing, including penetrant testing and magnetic particle testing.

The foregoing object of the invention is preferably realized by providing an eddy current or phased array instrument with a color palette module that allows the deployment of an array of color representation system typically used in traditional non-electronic testing methods.

In accordance to various embodiments of instrument and method of the present disclosure, the kinds of color palette employed by a specific instrument can vary depending on how many and what kind of traditional testing the instrument is tasked to emulate.

BRIEF DESCRIPTION OF THE DRAWING(S)

The patent or application file contains at least one drawing executed in color. Copies of this patent or patent application publication with color drawing(s) will be provided by the Office upon request and payment of the necessary fee.

DETAILED DESCRIPTION OF PREFERRED EMBODIMENT

Figure 1:
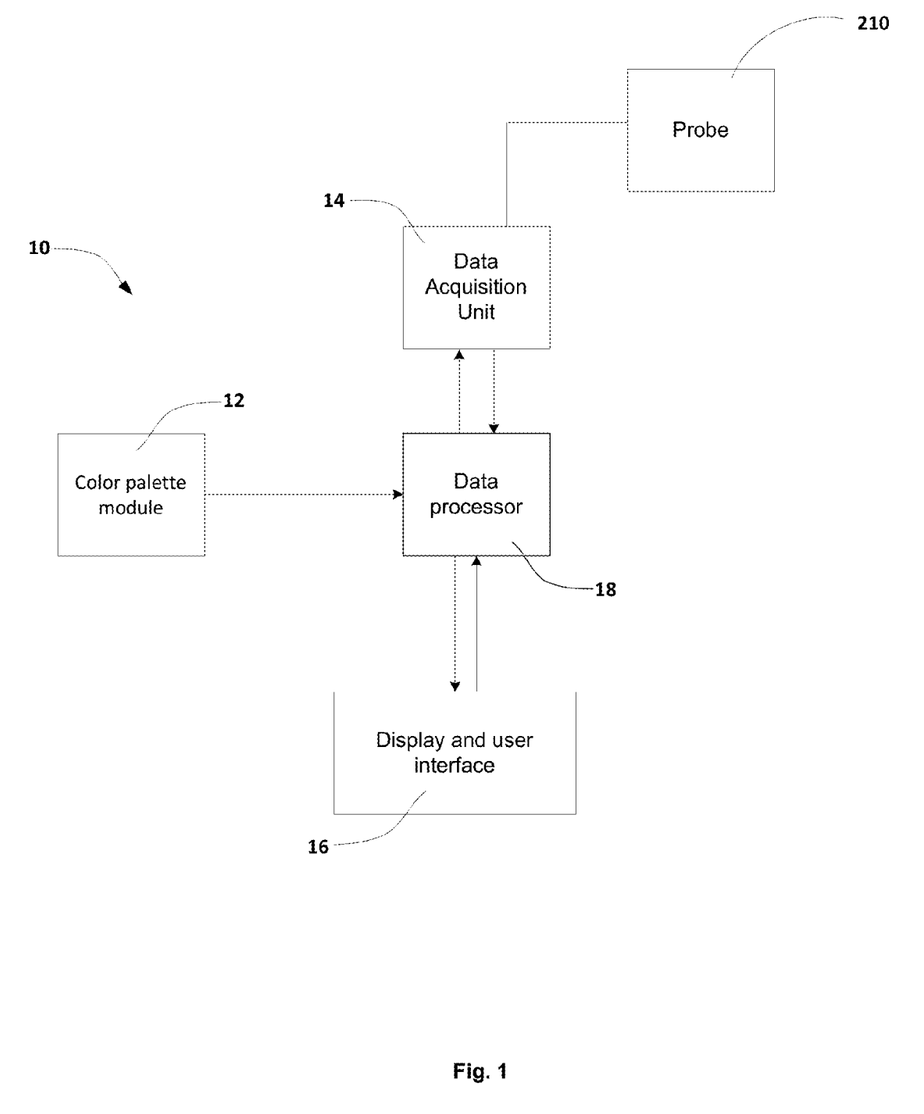
FIG. 1 is a schematic view of the inspection system including a color palette module according to the preferred embodiment.

Referring to FIG. 1, the presently disclosed inspection instrument, such as an eddy current device 10 embodies a color palette module 12 either being coupled or integrated with a data processor 18. The eddy current device also embodies a data acquisition unit 14, the data processor 18, a probe 210 and a display and user interface unit 16. It should be noted that data acquisition unit 14, data processor 18, probe 210 and display 16 can all be part of an otherwise existing inspection system. Color palette module 12 represents one of the novel aspects of the present disclosure.

It should be noted that color rendering does exist in conventional NDT/NDI devices. However, they do not embody a color module containing color palette names that systematically and closely emulating those of used in traditional non-electronic testing.

Continuing with FIG. 1, in the preferred embodiment, color palette module 12 is preferably configured to contain a color tagging system to assign a corresponding RGB value to each of the amplitude markers, which are a series of amplitude percentage values that concerns the inspection operation. The basic color tagging system for this specific color palette name is shown in Table-1 as follows with color palette name "PT/Visible/Red Dye with Pink Shades". It should be noted that the first column of Table-1 are "amplitude markers" named as such to be matched with corresponding signal amplitude shown in column 2. The marking of the amplitude is the same or significantly similar to that used in traditional testing. In columns 3~5, RGB values are given corresponding to a specific marker and according to the convention of traditional testing.

Figure 3:
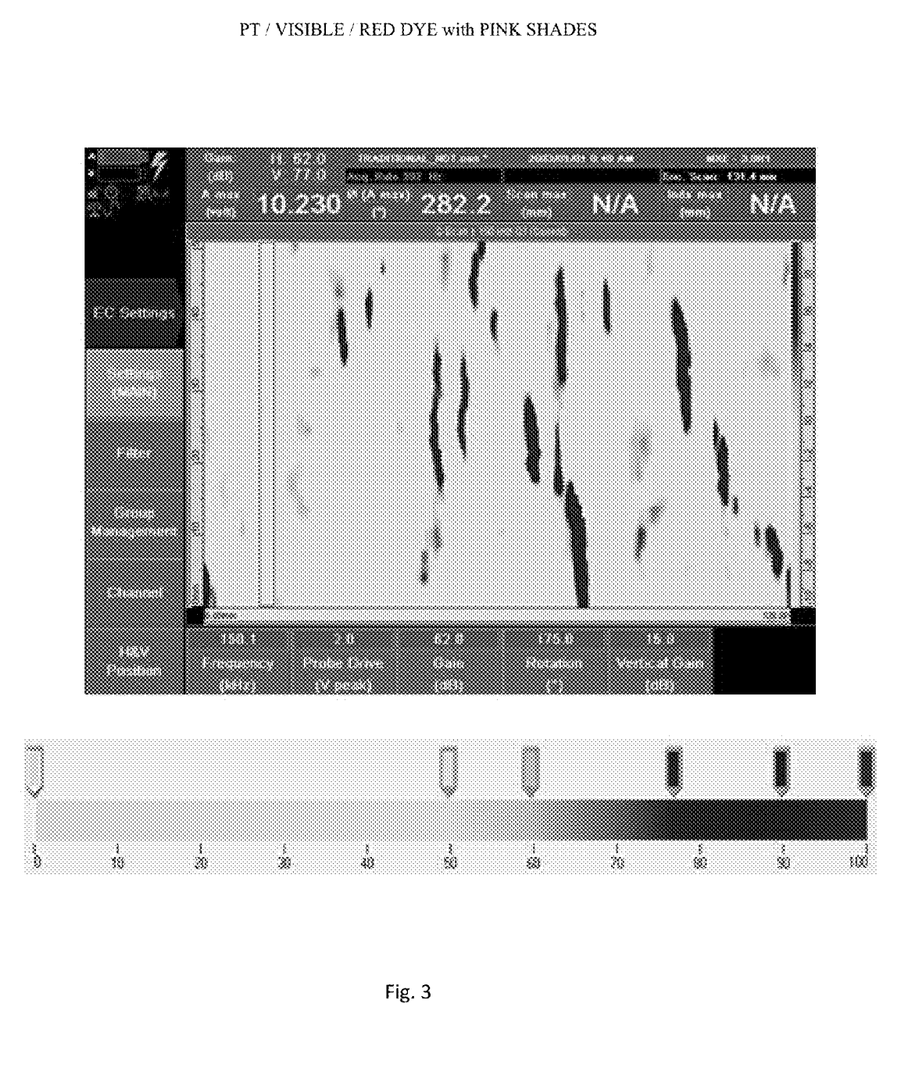
FIG. 3 is a color display resulted from the execution of the color palette module according to the preferred embodiment, showing an eddy current inspection C-scan result emulating the PT/VISIBLE/RED DYE with PINK SHADES color palette. The corresponding RGB values are shown in Table-1.

An exemplary testing result presented according to the RGB values in Table-1 is shown in FIG. 3.

TABLE 1

RGB Values for Corresponding Markers for Palette
Name PT/Visible/Red Dye with Pink Shades

| Amplitude Marker Point | % vertical amplitude | RED | GREEN | BLUE |
|---|---|---|---|---|
| Bottom | 0% | 204 | 204 | 204 |
| Good Test | 50% | 224 | 224 | 224 |
| Halo | 60% | 229 | 165 | 245 |
| Transition | 77% | 97 | 11 | 15 |
| Bad test | 90% | 75 | 11 | 19 |
| Top | 100% | 127 | 9 | 15 |

It should be noted that Table-1 is of a color palette name called "PT/Visible/Red Dye with Pink Shades", often used by tradition penetrant testing visible with pink shades. The color display of this palette is shown in FIG. 3. More color palette names can be called by the NDT/NDI devices, determined by the operator.

Figure 2:
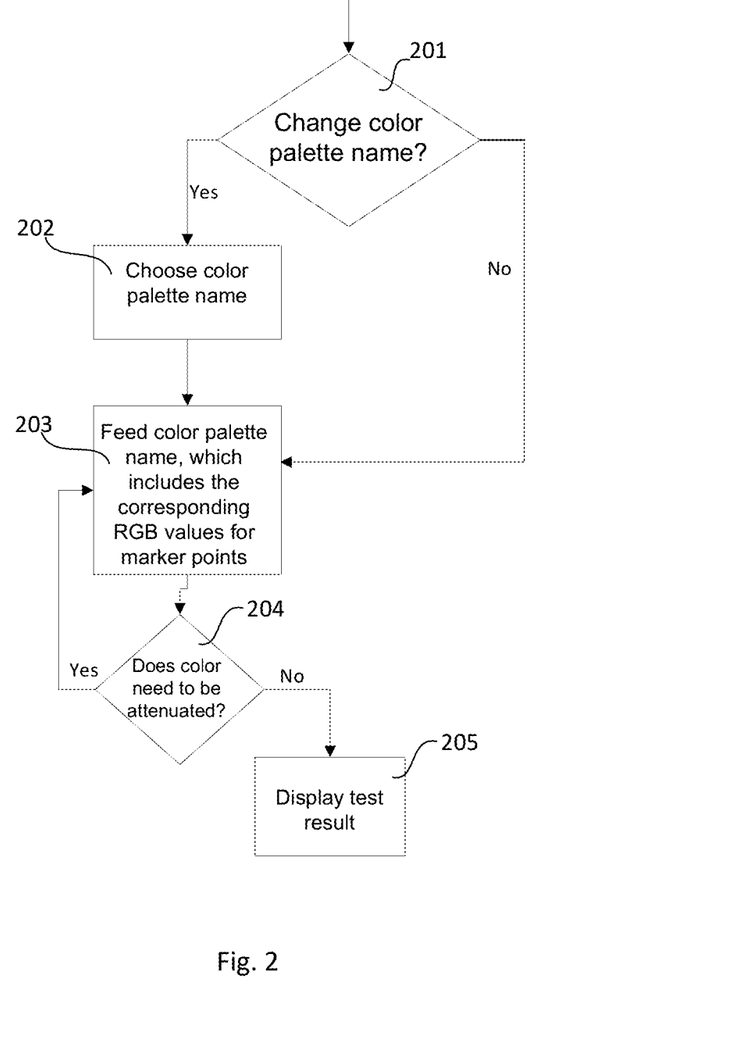
FIG. 2 is a flowchart showing the exemplary steps executed by the usage of the color palette module.

Reference now is made to FIG. 2, which is an exemplary routine of color palette module 12 executable by a processor or processor 18.

Preferably, at the beginning of an inspection operation, the operator is provided at step 201 the color palette name used in last inspection via user interface, and prompted whether to change the existingly loaded color palette name. Once a color palette name, such as that of "PT/Visible/Red Dye with Pink Shades" shown in Table-1 and FIG. 3 is selected in step 202, the selected color palette name is called by the program and color palette module 12 provides the corresponding RGB values to processor 18 in step 203. Processor 18 matches the measure amplitude for each data sample and assigns corresponding RGB values according to Table-1 to instruct display 16 to display in step 205.

According to FIG. 2, optionally, color module 12 can also embody a step that allows the operation to adjust the contrast of the color presentation in step 204. The step can also be called "color attenuation", which allows the adjustment of the "top" and the "bottom" of the color scale (shown in FIGS. 3~6).

As can be seen from Table-1 and FIG. 3, the preferred process to display the colors is using a color palette system made of linear gradients, associated to the measurement signal amplitude. The preferred example is using a palette that emulates the visible penetrant testing (PT) method with red dye in pink shades.

Expanding from Table-1, more color palette names typically used in traditional testing are introduced in Table-2. As can be seen in Table-2, the first column is a collection of color palette names typically used in traditional testing which are preferably preloaded in an NDT/NDI instrument according to the present disclosure. As can be seen in Table-2, column-1 provides a series of "palette names" or palette schemes, closely matching those commonly used in PT and MP conventional operations. The presently disclosed system and method, for each palette scheme (or palette name) provides a series of displaying RGB values for each corresponding measurement result represented as amplitude in the form of percentage of the full amplitude. The match of the RGB values with amplitude is a close representation of the color assigning system used by respective traditional testing, as listed in column-1.

Columns 2-7 are the amplitude markers used in the same way as those in Table-1, and follow the conventions used in traditional testing, such as PT testing.

The last column lists the figure numbers showing the NDT device measurement result display using the corresponding color tagging system shown in the respective rows.

TABLE 2

Color Palette System Emulating Typical Traditional Testing
Values in the three number group are R/G/B Values
Values in percentage are marker amplitude percentage
Marker Point Names
R/G/BValues

| | Marker Points | | | | | | |
|---|---|---|---|---|---|---|---|
| Color Palette Names | Bottom | Good Test | Halo | Transition | Bad test | Top | FIG. # |
| PT-visible (red dye) | 204/204/204 0% | 224/224/224 10% | N/A | 224/224/224 55% | 157/7/14 66% | 59/11/21 100% | Not shown in drawings |
| PT-fluorescent (blue/green) | 0/75/244 0% | 2/68/218 20% | N/A | 11/37/95 60% | 95/237/1 70% | 172/252/0 100% | 4 |
| PT-fluorescent (purple/blue) | 175/5/173 0% | 114/10/118 20% | N/A | 22/10/110 60% | 13/247/255 70% | 185/243/245 100% | Not shown in drawings |
| MP-fluorescent (purple shades) | 131/9/110 0% | 42/10/122 22% | 89/72/11 54% | 95/237/1 62% | N/A | 172/252/0 100% | 5 |
| MP-fluorescent (blue shades) | 7/2/210 0% | 17/8/136 20% | 35/71/11 53% | 95/237/1 62% | N/A | 172/252/0 100% | Not shown in drawings |

TABLE 2-continued

Color Palette System Emulating Typical Traditional Testing
Values in the three number group are R/G/B Values
Values in percentage are marker amplitude percentage
Marker Point Names
R/G/BValues

| | Marker Points | | | | | | |
|---|---|---|---|---|---|---|---|
| Color Palette Names | Bottom | Good Test | Halo | Transition | Bad test | Top | FIG. # |
| MP-visible (red powder) | 223/223/223 0% | 240/240/240 20% | 241/241/241 50% | 128/128/128 58% | 133/29/3 66% | 140/8/52 100% | 6 |
| MP-visible (black powder) | 243/245/199 0% | 250/250/250 20% | N/A | 241/241/241 55% | 64/64/64 70% | 0/0/0 100% | Not shown in drawings |

Figure 4:
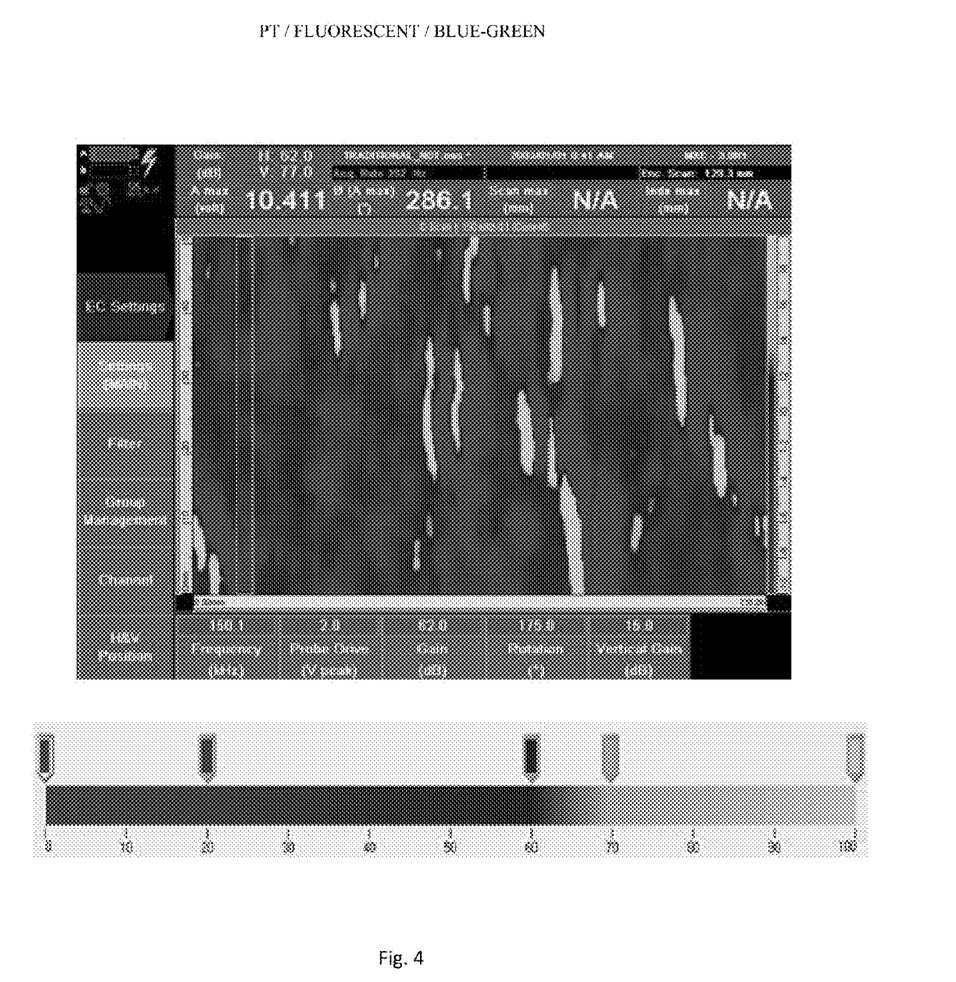
FIG. 4 is a color display according to an alternate embodiment, showing an eddy current inspection C-scan result emulating the PT/FLUORESCENT/BLUE-GREEN color palette.
Figure 5:
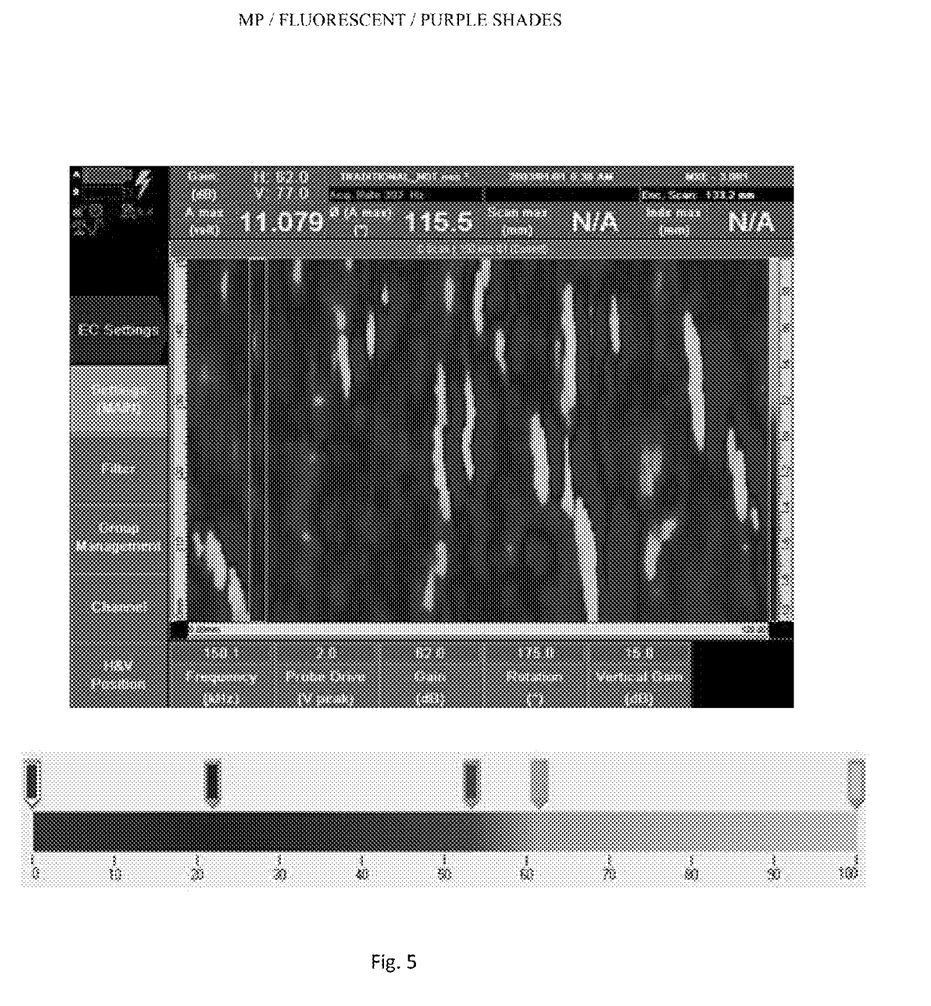
FIG. 5 is a color display according to an alternate embodiment, showing an eddy current inspection C-scan result emulating the MP/FLUORESCENT/PURPLE SHADES color palette.
Figure 6:
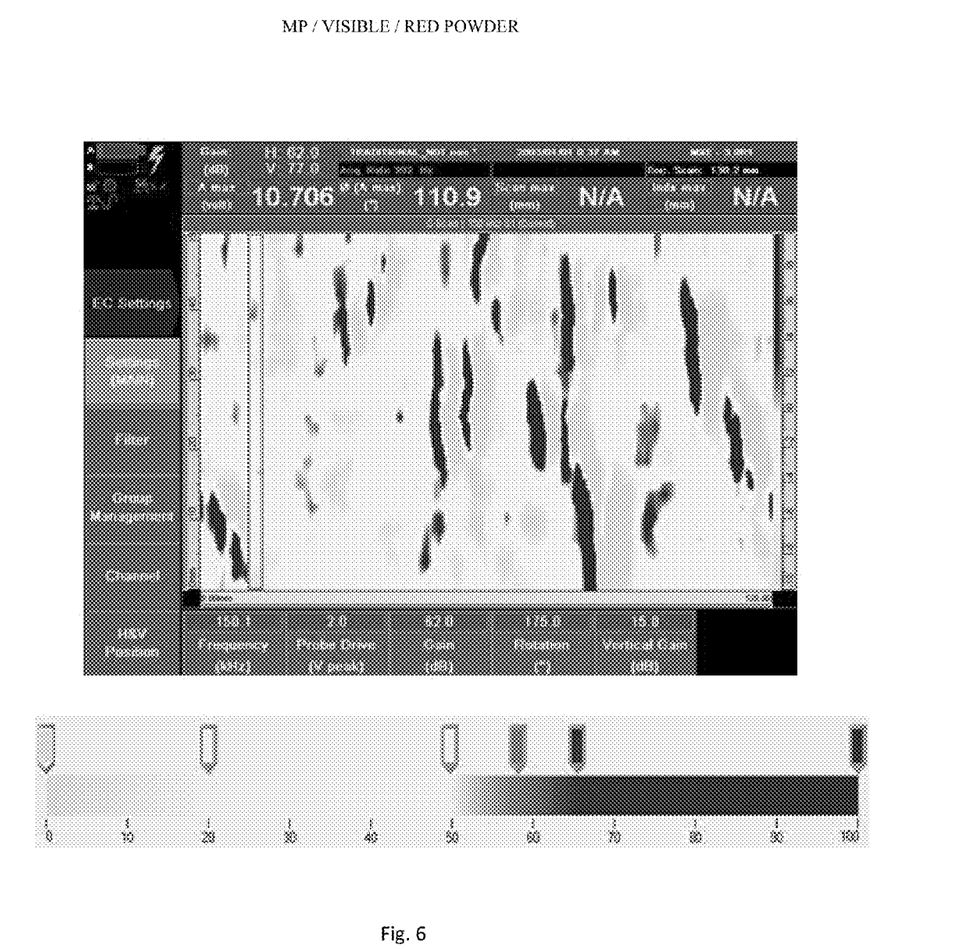
FIG. 6 is a color display according to an alternate embodiment, showing an eddy current inspection C-scan result emulating the MP/VISIBLE/RED POWDER color palette.

In each of the following figures of FIGS. 4~6, the results of vertical amplitude of the ECA signals are displayed in a 2-dimensional "C-scan image" as colors according to corresponding "color names" shown in Table-2. The image of each of FIGS. 4~6 shows the direct relation between the signal vertical amplitude and the color palette, according to the corresponding color palette name. As can be seen, for example, the result shown in FIG. 3 is an image that looks very similar to the penetrant testing results.

FIG. 4 is a color display of an exemplary testing result shown in C-scan, emulating the PT/FLUORESCENT/BLUE-GREEN color palette using the respective RGB values for each marker point shown in Table-2 with corresponding palette name.

FIG. 5 is a color display of an exemplary testing result shown in C-scan, emulating the MP/FLUORESCENT/PURPLE SHADES palette using the respective RGB values for each marker point shown in Table-2 with corresponding palette name.

FIG. 6 is of an exemplary testing result shown in C-scan, emulating the MP/VISIBLE/RED POWDER color palette using the respective RGB values for each marker point shown in Table-2 with corresponding palette name.

Other palette names for each of the traditional NDT methods herein to be replaced using the present disclosure are also represented in Table-2. The colors are represented as R/G/B and the marker points in vertical amplitude (% full scale).

It should be appreciated that color tagging to vertical amplitude values can be readily applied to a color tagging (naming) system to other measurement values, such as horizontal amplitude values, magnitude values, which are all within the scope and framework of the present disclosure.

It should also be appreciated that the color tagging system herein presented can be readily applied to normalized or converted signal, such as values relative to an adjustable ECA null point, and should be considered within the scope of the present disclosure.

It should also be appreciated that the color tagging system herein presented can be readily applied to normalized or converted signal, such as those resulted from differential probes, and should be considered within the scope of the present disclosure. In such cases, the corresponding RGB values simply need to be applied to marker points for normalized or converted signal values.

What is claimed is:
1. A non-destructive testing or inspection (NDT/NDI) device configured for inspecting a test object, and providing a display of measurement results, the device comprises:
   a data acquisition unit,
   a data processor, including a color palette module, a colored display,
   wherein the data processor is configured to process input signals from the data acquisition unit, providing measurement values in a series of marker points, wherein the color palette module is operable to match a set of RGB (Red, Green and Blue) values for each of the corresponding marker points emulating a specific color used in at least one traditional non-electronic testing setup for the corresponding marker point,
   wherein the color palette further configured to choose a selected color palette name selected from one of the following color palette names related to the at least one traditional non-electronic testing setup, including a penetrant testing method (PT) or a magnetic particle method (MP), and comprising that listed in column one of Table-B, below,
   wherein the color palette module is further operable, under the selected color palette name, to match a set of R/G/B (Red, Green and Blue) values for each of the corresponding marker points substantially equivalent to that listed in Table-B,

TABLE B

Marker Point Names
R/G/B Values

| | Marker Points | | |
|---|---|---|---|
| Color Palette Names | Bottom | Good Test | Halo |
| PT-visible (red dye) | 204/204/204 0% | 224/224/224 10% | N/A |
| PT-fluorescent (blue/green) | 0/75/244 0% | 2/68/218 20% | N/A |
| PT-fluorescent (purple/blue) | 175/5/173 0% | 114/10/118 20% | N/A |
| MP-fluorescent (purple shades) | 131/9/110 0% | 42/10/122 22% | 89/72/11 54% |
| MP-fluorescent (blue shades) | 7/2/210 0% | 17/8/136 20% | 35/71/11 53% |
| MP-visible (red powder) | 223/223/223 0% | 240/240/240 20% | 241/241/241 50% |
| MP-visible (black powder) | 243/245/199 0% | 250/250/250 20% | N/A |

| | Marker Points | | |
|---|---|---|---|
| Color Palette Names | Transition | Bad test | Top |
| PT-visible (red dye) | 224/224/224 55% | 157/7/14 66% | 59/11/21 100% |
| PT-fluorescent (blue/green) | 11/37/95 60% | 95/237/1 70% | 172/252/0 100% |
| PT-fluorescent (purple/blue) | 22/10/110 60% | 13/247/255 70% | 185/243/245 100% |
| MP-fluorescent (purple shades) | 95/237/1 62% | N/A | 172/252/0 100% |

TABLE B-continued

| Marker Point Names R/G/B Values | | | |
|---|---|---|---|
| MP-fluorescent (blue shades) | 95/237/1 62% | N/A | 172/252/0 100% |
| MP-visible (red powder) | 128/128/128 58% | 133/29/3 66% | 140/8/52 100% |
| MP-visible (black powder) | 241/241/241 55% | 64/64/64 70% | 0/0/0 100% | and wherein the processor instructs the colored display to display the measurement values with the corresponding matched RGB values accordingly.

2. The device of claim 1, wherein the color palette module is further operable to adjust the scale of the measurement results.

3. The device of claim 1, wherein the color palette module is further operable with the measurement values to be based on a series of corresponding absolute values of amplitude indicative of a corresponding measurement result.

4. The device of claim 1, wherein the color palette module is further operable with measurement values to be based on normalized values in percentage of a reference amplitude.

5. The device of claim 1, wherein the color palette module is further operable with the measurement values to be based on exponentially normalized values.

6. The device of claim 1 is an eddy current device with array sensors.

7. The device of claim 1 is an ultrasonic phased array device.

8. The device of claim 1, wherein the color palette module in emulating the traditional non-electrical testing setup, is operable to match a set of RGB (Red, Green and Blue) values for each of the corresponding marker points to be equivalent to the RGB values listed in the Table A

TABLE A

| Marker Points | Measurement values | RED | GREEN | BLUE |
|---|---|---|---|---|
| Bottom | 0% | 204 | 204 | 204 |
| Good Test | 50% | 224 | 224 | 224 |
| Halo | 60% | 229 | 165 | 245 |
| Transition | 77% | 97 | 11 | 15 |
| Bad test | 90% | 75 | 11 | 19 |
| Top | 100% | 127 | 9 | 15. |

9. A method of providing color display for a non-destructive testing or inspection (NDT/NDI) device used for inspecting a test object, the method comprising steps of,
collecting input signals from inspecting the test object,
processing the input signals and providing measurement values in a series of marker points, matching a set of RGB (Red, Green and Blue) values for each of the corresponding marker points emulating a specific color used in at least one traditional non-electronic testing setup for the corresponding marker point,
selecting a selected color palette name from a series of color palette names referring to at least one traditional non-electronic testing setup, including a penetrant testing method (PT) and a magnetic particle method (MP), which are listed in column one of Table-C, below,
under the selected color palette name, matching a set of R/G/B (Red, Green and Blue) values for each of the corresponding marker points substantially equivalent to that listed in Table-C,

TABLE C

| | Marker Point Names R/G/B Values | | | | | |
|---|---|---|---|---|---|---|
| | Marker Points | | | | | |
| Color Pallette Names | Bottom | Good Test | Halo | Transition | Bad test | Top |
| PT-visible (red dye) | 204/204/204 0% | 224/224/224 10% | N/A | 224/224/224 55% | 157/7/14 66% | 59/11/21 100% |
| PT-fluorescent (blue/green) | 0/75/244 0% | 2/68/218 20% | N/A | 11/37/95 60% | 95/237/1 70% | 172/252/0 100% |
| PT-fluorescent (purple/blue) | 175/5/173 0% | 114/10/118 20% | N/A | 22/10/110 60% | 13/247/255 70% | 185/243/245 100% |
| MP-fluorescent (purple shades) | 131/9/110 0% | 42/10/122 22% | 89/72/11 54% | 95/237/1 62% | N/A | 172/252/0 100% |
| MP-fluorescent (blue shades) | 7/2/210 0% | 17/8/136 20% | 35/71/11 53% | 95/237/1 62% | N/A | 172/252/0 100% |
| MP-visible (red powder) | 223/223/223 0% | 240/240/240 20% | 241/241/241 50% | 128/128/128 58% | 133/29/3 66% | 140/8/52 100% |
| MP-visible (black powder) | 243/245/199 0% | 250/250/250 20% | N/A | 241/241/241 55% | 64/64/64 70% | 0/0/0 100% | using the matched R/G/B values to display color for the measurement values.

10. The method of claim 9, wherein the color palette module is further operable to adjust the scale of the measurement results.

11. The method of claim 9, wherein the color palette module is further operable with the measurement values to be based on a series of corresponding absolute values of amplitude indicative of a corresponding measurement result.

12. The method of claim 9, wherein the color palette module is further operable with the measurement values to be based on normalized values in percentage of a reference amplitude.

13. The method of claim 9, wherein the color palette module is further operable with the measurement values based on exponentially normalized values.

14. The method of claim 9, wherein the device is an eddy current inspection device with array sensors.

15. The method of claim 14, wherein the device is an ultrasonic phased array device.

16. The method of claim 9, wherein the color palette module is further operable to adjust the scale of the measurement results.

17. The method of claim 9, wherein the color palette module is further operable with the measurement values to be based on a series of corresponding absolute values of amplitude indicative of a corresponding measurement result.

18. The method of claim 9, wherein the color palette module is further operable with the measurement values to be based on normalized values in percentage of a reference amplitude.

19. The method of claim 9, wherein the color palette module is further operable with the measurement values based on exponentially normalized values.

\* \* \* \* \*